(12) United States Patent
Chen et al.

(10) Patent No.: US 10,759,779 B2
(45) Date of Patent: Sep. 1, 2020

(54) CRYSTALLINE FORM OF OREXIN RECEPTOR ANTAGONIST, PROCESSES FOR PREPARATION THEREOF AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Chunxiang Huang, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/777,121

(22) Filed: Jan. 30, 2020

(65) Prior Publication Data

US 2020/0190060 A1    Jun. 18, 2020

Related U.S. Application Data

(63) Continuation of application No. PCT/CN2018/097797, filed on Jul. 31, 2018.

(30) Foreign Application Priority Data

Aug. 1, 2017 (CN) .......................... 2017 1 0648135

(51) Int. Cl.
*C07D 401/12* (2006.01)
(52) U.S. Cl.
CPC ........ *C07D 401/12* (2013.01); *C07B 2200/13* (2013.01)
(58) Field of Classification Search
CPC .................................................. C07D 401/12
See application file for complete search history.

(56) References Cited

U.S. PATENT DOCUMENTS 8,268,848 B2    9/2012    Terauchi et al.
10,172,824 B2   1/2019    Wang et al.

FOREIGN PATENT DOCUMENTS

WO    2013/123240 A1    8/2013
WO    2016/063995 A1    4/2016

OTHER PUBLICATIONS

International Search Report for Application No. PCT/CN2018/097797, dated Oct. 31, 2018, 6 pages.

*Primary Examiner* — Paul V Ward
(74) *Attorney, Agent, or Firm* — McCarter & English, LLP; Steven G. Davis; Wei Song

(57) ABSTRACT

The present disclosure provides a novel crystalline form of Lemborexant and processes for preparation thereof. Pharmaceutical composition containing Lemborexant, and use of Lemborexant for preparing orexin receptor antagonist drug, and use of Lemborexant for preparing drugs treating insomnia and irregular sleep-wake rhythm disorder are also provided. The crystalline form of the present disclosure have one or more improved properties compared with crystalline forms of prior arts, and has significant values for future drug optimization and development.

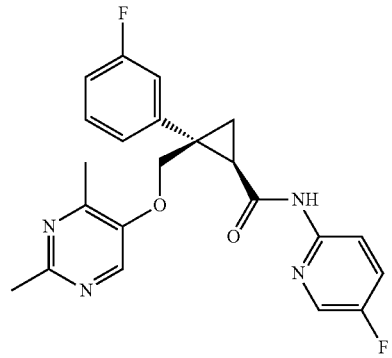

Compound (I)

8 Claims, 7 Drawing Sheets

CRYSTALLINE FORM OF OREXIN RECEPTOR ANTAGONIST, PROCESSES FOR PREPARATION THEREOF AND USE THEREOF

CROSS-REFERENCE TO RELATED APPLICATIONS

This application is a continuation of International Application No. PCT/CN2018/097797, filed on Jul. 31, 2018, which claims the benefit of foreign priority of Chinese Patent Application No.: 201710648135.2, filed on Aug. 1, 2017. The entire contents of the aforementioned applications are incorporated herein by reference.

TECHNICAL FIELD

The present disclosure relates to the field of pharmaceutical chemistry, particularly relates to a novel crystalline forms of orexin receptor antagonist, processes for preparation and use thereof.

BACKGROUND

E-2006 (Lemborexant) was developed by Eisai and clinically used to treat insomnia. Studies have shown that the orexin system is a key regulator of the sleep-wake cycle, and thus orexin receptor antagonists have the potential to counteract inappropriate nighttime wakefulness and promote a regular sleep-wake cycle. E-2006 is an orexin receptor antagonist. In clinical trials, E-2006 can significantly improve sleep efficiency in patients with insomnia, including falling asleep fast and shorter time spent awake at night. In addition, E-2006 also shows great potential in the treatment of Alzheimer's patients with Irregular Sleep-Wake Rhythm Disorder (ISWRD). ISWRD is different from common insomnia, and has unmet clinical needs.

The chemical name of E-2006 is (1R,2S)-2-{[(2,4-dimethylpyrimidin-5-yl)oxy]methyl}-2-(3-fluorophenyl)-N-(5-fluoropyridin-2-yl)cyclopropanecarboxamide (hereinafter referred to as "Compound (I)"), and the structure is shown as follows:

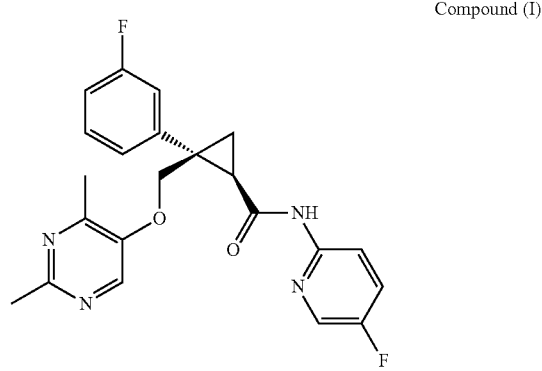 [SMILES: Cc1ncc(OC[C@@]2(c3cccc(F)c3)C[C@H]2C(=O)Nc2ccc(F)cn2)c(C)n1]

Compound (I)

Currently, no crystalline forms of compound (I) was disclosed. CN103153963B disclosed the structure of compound (I) and the process for preparing compound (I). The inventors of the present disclosure have repeated the preparation method in CN103153963B and amorphous solid was obtained. Compared with the crystalline form of the present disclosure, the amorphous solid has lower stability, lower density and poorer flowability, which is not suitable for the preparation of drug product. In addition, amorphous is the thermodynamically most unstable solid form, which is prone to crystal transformation or chemical degradation, resulting in a decrease in the purity of the compound. The preparation of amorphous is usually a rapid precipitation process to produce kinetically stable solid, which easily leads to excessive residual solvent. The particle property control in the preparation process is difficult.

The inventors of the present disclosure discovered excellent crystalline form CS2 of compound (I), which has advantages in at least one aspect of stability, melting point, solubility, in vitro and in vivo dissolution, hygroscopicity, bioavailability, adhesiveness, compressibility, flowability, processability, purification ability, formulation production, etc. Particularly, crystalline form CS2 has good stability, low hygroscopicity, good formulation processability, high in vitro dissolution and dissolution rate, which provides a new and better choice for the development of drug containing compound (I) and is of great significance.

SUMMARY

The main objective of the present disclosure is to provide a novel crystalline form of compound (I), processes for preparation and use thereof.

According to the objective of the present disclosure, crystalline form CS2 of compound (I) is provided (hereinafter referred to as Form CS2).

According to one aspect of the present disclosure, the X-ray powder diffraction pattern of Form CS2 shows characteristic peaks at 2theta values of 7.8°±0.2°, 15.6°±0.2° and 11.4°±0.2° using CuKα radiation.

Furthermore, the X-ray powder diffraction pattern of Form CS2 shows one or two or three characteristic peaks at 2theta values of 12.5°±0.2°, 21.3°±0.2°, 27.3°±0.2°. Preferably, the X-ray powder diffraction pattern of Form CS2 shows three characteristic peaks at 2theta values of 12.5°±0.2°, 21.3°±0.2°, 27.3°±0.2°.

Furthermore, the X-ray powder diffraction pattern of Form CS2 shows one or two or three characteristic peaks at 2theta values of 24.0°±0.2°, 19.4°±0.2° and 22.3°±0.2°. Preferably, the X-ray powder diffraction pattern of Form CSI shows three characteristic peaks at 2theta values of 24.0°±0.2°, 19.4°±0.2°, 22.3°±0.2°.

According to another aspect of the present disclosure, the X-ray powder diffraction pattern of Form CS2 shows three or four or five or six or seven or eight or nine or ten or eleven characteristic peaks at 2theta values of 7.8°±0.2°, 15.6°±0.2°, 11.4°±0.2°, 12.5°±0.2°, 21.3°±0.2°, 27.3°±0.2°, 24.0°±0.2°, 19.1°±0.2°, 19.4°±0.2°, 22.3°±0.2°, 25.9°±0.2° using CuKα radiation.

Without any limitation being implied, the X-ray powder diffraction pattern of Form CS2 is substantially as depicted in FIG. 1 or 5.

According to the objective of the present disclosure, a process for preparing Form CS2 is also provided. The process comprises:

(1) Dissolving compound (I) in a solvent to get a solution containing compound (I), then adding an anti-solvent to the solution slowly, stirring and crystallizing to obtain Form CS2; or (2) Dissolving compound (I) in ketones and slowly evaporating to obtain Form CS2; or (3) Dissolving compound (I) in nitriles, adding an ionic liquid, then slowly evaporating to obtain Form CS2.

Furthermore, in method (1) said solvent is alcohol, said anti-solvent is water;

Furthermore, in method (1) said alcohol is methanol.

Furthermore, in method (2) said ketone is preferably acetone.

Furthermore, in method (3) said nitrile is preferably acetonitrile, said ionic liquid is preferably 1-ethyl-3-methylimidazolium methyl sulfate, or 1-ethyl-3-methylimidazolium hexafluoroantimonate or 1,3-dimethylimidazolium dimethyl phosphate.

According to the objective of the present disclosure, a pharmaceutical composition is provided, said pharmaceutical composition comprises a therapeutically effective amount of Form CS2 and pharmaceutically acceptable carriers, diluents or excipients.

Furthermore, Form CS2 can be used for preparing orexin receptor antagonist drugs.

Furthermore, Form CS2 can be used for preparing drugs treating insomnia and/or irregular sleep-wake rhythm disorder.

Form CS2 of the present disclosure has the following advantages:

(1) Form CS2 of the present disclosure has lower hygroscopicity. The test results show that the weight gain of Form CS2 at 80% RH (Relative Humidity) is 0.21%. Form CS2 is slightly hygroscopic. The crystalline form does not change after DVS, Form CS2 has good physical stability at 0-95% RH.

Hygroscopicity affects the stability of drug substances, flowability and uniformity during the formulation process, thus affecting the quality of drug products. Hygroscopicity affects the preparation, storage and post-treatment of the drug. The crystalline form with low hygroscopicity is not demanding on storage conditions, which reduces the cost of storage and quality control, and has strong economic value.

(2) The crystalline form provided by the present disclosure has good stability.

Drug substance Form CS2 of the present disclosure has good physical and chemical stability in different storage conditions. The crystalline form of Form CS2 of the present disclosure remained unchanged for at least 10 months when stored in open dishes under the conditions of 25° C./60% RH and 40° C./75% RH, preferably for at least one year. The crystalline form of Form CS2 doesn't change for at least 2 weeks when stored under the condition of 60° C./75% RH. The chemical purity of Form CS2 of the present disclosure is above 99%, preferably above 99.5%, and remained substantially unchanged during storage.

Form CS2 of the present disclosure has good physical stability after grinding. Grinding and pulverization are often required in drug manufacturing process. Good physical stability of the drug substance can reduce the risk of crystallinity decrease and crystal transformation during the drug production process.

Form CS2 of the present disclosure has good physical and chemical stability in drug product. Drug product is prepared with excipient and stored under the conditions of 25° C./60% RH and 40° C./75% RH for at least one month. The crystalline form of Form CS2 remained unchanged and chemical purity remained substantially unchanged in drug product.

Drug substance and drug product has good physical and chemical stability. During the storage and formulation process, Form CS2 does not convert to other crystalline forms, and the chemical purity of Form CS2 remained substantially unchanged during storage, thus ensuring consistent and controllable quality of drug substance and drug product.

(3) Form CS2 has good in vitro dissolution and dissolution rate. Form CS2 of the present disclosure in drug product underwent 100% dissolution in 60 minutes in 0.1 mol/L aqueous hydrochloric acid solution. Good in vitro dissolution leads to higher in vivo absorption, thereby achieving ideal bioavailability.

Dissolution is the prerequisite for absorption. Good in vitro dissolution leads to higher in vivo absorption and better in vivo exposure, thereby improving drug's bioavailability and efficacy. High dissolution rate is beneficial for the drug to achieve peak plasma concentration quickly after administration, thus ensuring rapid drug action.

Furthermore, Form CS2 of the present disclosure also has the following advantages:

(1) Form CS2 of the present disclosure has good compressibility. Failure in hardness/friability test issue can be avoided in the tableting process due to better compressibility of Form CS2, thus reducing the requirements for pretreatment process, making the preparation process more reliable and improving product appearance and product quality.

(2) Compared with prior art, Form CS2 of the present disclosure has higher density. Test results indicate that the bulk density and tapped density of Form CS2 are remarkably higher than that of prior art solid. Higher density of Form CS2 is beneficial to large scale production. High density of Form CS2 can also reduce dust, reduce occupational hazard, reduce security risks and ensure production safety.

(3) Compared with prior art, Form CS2 of the present disclosure has better flowability. Flowability evaluation results indicate that the flowability of Form CS2 is good, while the flowability of prior art form is poor. Better flowability can effectively increase the speed of tableting and filling and increase manufacturing efficiency. Better flowability of Form CS2 ensures the blend uniformity and content uniformity of the drug product, and reduces the weight variation of the drug product and improves product quality.

(4) Compared with prior art, Form CS2 of the present disclosure shows superior adhesiveness. Adhesiveness evaluation results indicate that Form CS2 has low adhesiveness amount and low adhesiveness. Due to low adhesiveness of Form CS2, adhesion to roller and tooling during dry-granulation and compression process can be reduced, which is also beneficial to improve product appearance and weight variation. In addition, low adhesiveness of Form CS2 can reduce the agglomeration of drug substance, which is beneficial to the dispersion of drug substance and reduce the adhesion between drug substance and other excipients, and improve the blend uniformity and content uniformity of drug product.

(5) Form CS2 of the present disclosure has almost no residual solvent and meets the requirements of drug substance, while the residual solvent of the prior art exceeds the standard and cannot be used as a drug substance directly. Many organic solvents are harmful to human and environment. Therefore, in order to ensure drug safety and product quality, it is necessary to control the residual organic solvent of drug substance.

In the present disclosure, said "evaporating" is accomplished by using a conventional method in the field such as slow evaporation or rapid evaporation. Slow evaporation is accomplished in a container covered by sealing film with pinholes. Rapid evaporation is accomplished in an open container.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS2 of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the number of shift ranges expected by one of skilled in the art is represented by the term "about".

DETAILED DESCRIPTION

Figure 1:
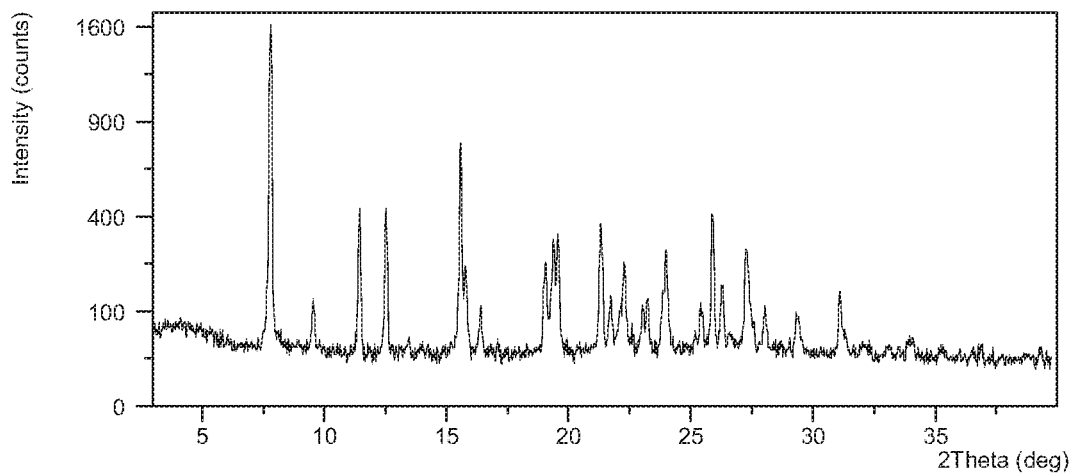
FIG. 1 shows an XRPD pattern of Form CS2 in Example 1.

The present disclosure is further illustrated by the following examples which describe the preparation and use of the crystalline form of the present disclosure in detail. It is obvious to those skilled in the art that many changes in the materials and methods can be accomplished without departing from the scope of the present disclosure.

The abbreviations used in the present disclosure are explained as follows:
XRPD: X-ray Powder Diffraction
DSC: Differential Scanning calorimetry
TGA: Thermo Gravimetric Analysis
DVS: Dynamic Vapor Sorption
$^1$H NMR: Proton Nuclear Magnetic Resonance
Instruments and methods used for data collection:
X-ray powder diffraction patterns in the present disclosure were acquired by a Bruker D2 PHASER X-ray powder diffractometer. The parameters of the X-ray powder diffraction method of the present disclosure were as follows:
X-ray Reflection: Cu, Kα
Kα1 (Å): 1.54060; Kα2 (A): 1.54439
Kα2/Kα1 intensity ratio: 0.50
Voltage: 30 (kV)
Current: 10 (mA)
Scan range: from 3.0 degree to 40.0 degree
Differential scanning calorimetry (DSC) data in the present disclosure were acquired by a TA Q2000. The parameters of the DSC method of the present disclosure are as follows:
Heating rate: 10° C./min
Purge gas: nitrogen
Thermo gravimetric analysis (TGA) data in the present disclosure were acquired by a TA Q500. The parameters of the TGA method of the present disclosure were as follows:
Heating rate: 10° C./min
Purge gas: nitrogen
Dynamic Vapor Sorption (DVS) is measured via a SMS (Surface Measurement Systems Ltd.) intrinsic DVS instrument. Typical Parameters for DVS test are as follows:
Temperature: 25° C.
Gas and flow rate: $N_2$, 200 mL/min
dm/dt: 0.002%/min
RH range: 0% RH to 95% RH
High Performance Liquid Chromatography (HPLC) data in the present disclosure were collected from an Agilent 1260 with Diode Array Detector (DAD).

The HPLC method parameters in the present disclosure are as follows:

Column: ZORBAX Eclipse C18, 100×4.6 mm, 5 μm

Mobile Phase: A: Acetonitrile:Water:Trifluoroacetic acid=50:950:1 (Volume ratio) B: 0.1% Trifluoroacetic acid in acetonitrile Gradient:

| Time (min) | % B |
|---|---|
| 0.0 | 0 |
| 0.5 | 0 |
| 30.0 | 90 |
| 35.0 | 90 |
| 35.1 | 0 |
| 40.0 | 0 |

Flow rate: 1.0 mL/min

Injection Volume: 2 μL

Detection wavelength: 220 nm

Column Temperature: 40° C.

Diluent: Acetonitrile

Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

Unless otherwise specified, the following examples were conducted at room temperature. Said "room temperature" is not a specific value, and refers to 10-30° C.

According to the present disclosure, compound (I) used as a raw material is solid (crystalline or amorphous), semisolid, wax or oil. Preferably, said compound (I) used as a raw material is a solid.

Raw materials of E-2006 used in the following examples were prepared by known methods in the prior art, for example, the method disclosed in CN103153963B.

DETAILED DESCRIPTION

Example 1 Preparation of Form CS2

Approximately 199.6 mg of compound (I) was weighted and dissolved in 3.0 mL of acetone, followed by filtration and slowly evaporation to obtain a solid at room temperature. The obtained solid was confirmed to be Form CS2. The XRPD pattern is substantially as depicted in FIG. 1, and the XRPD data are listed in Table 1.

Figure 2:
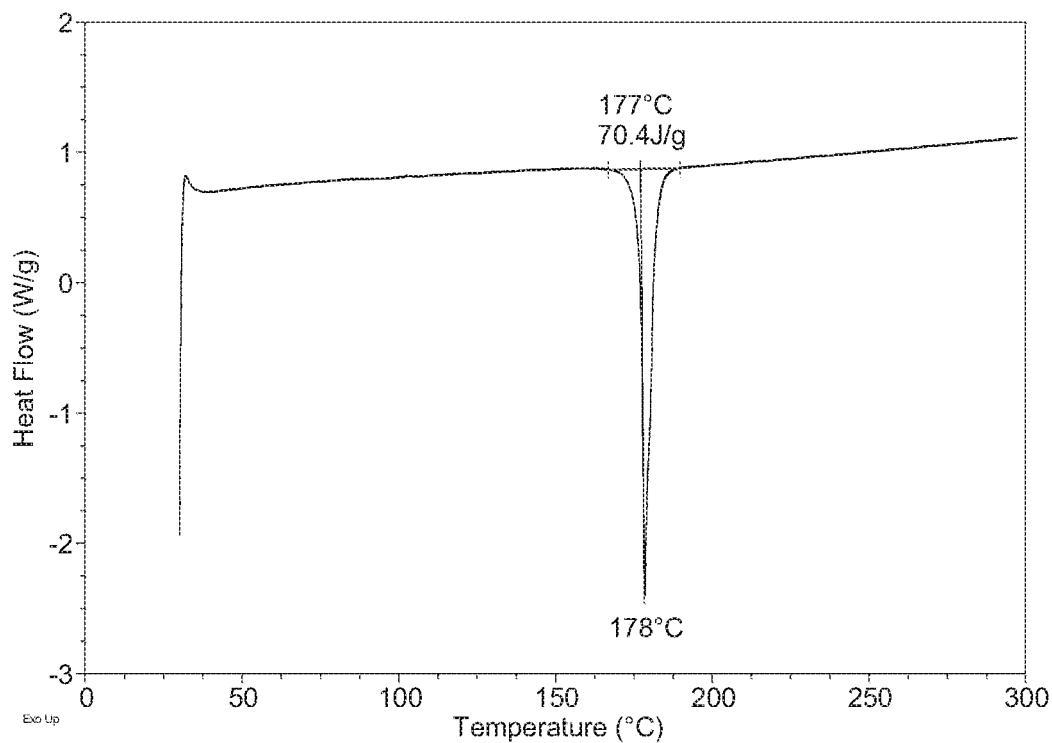
FIG. 2 shows a DSC curve of Form CS2 in Example 1.

The DSC curve of Form CS2 in this example is substantially as depicted in FIG. 2. When heated to 177° C., an endothermic peak appears, which corresponds to the melting endothermic peak of Form CS2.

Figure 3:
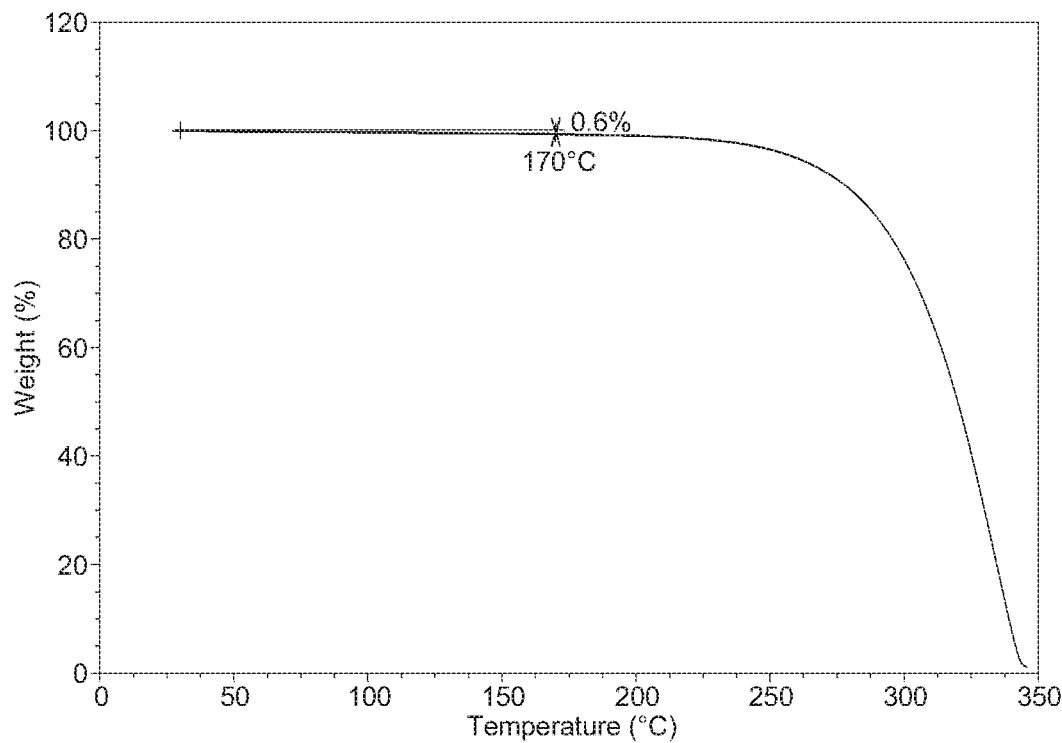
FIG. 3 shows a TGA curve of Form CS2 in Example 1.

The TGA curve of Form CS2 in this example shows about 0.6% weight loss when heated to 170° C., which is substantially as depicted in FIG. 3.

Figure 4:
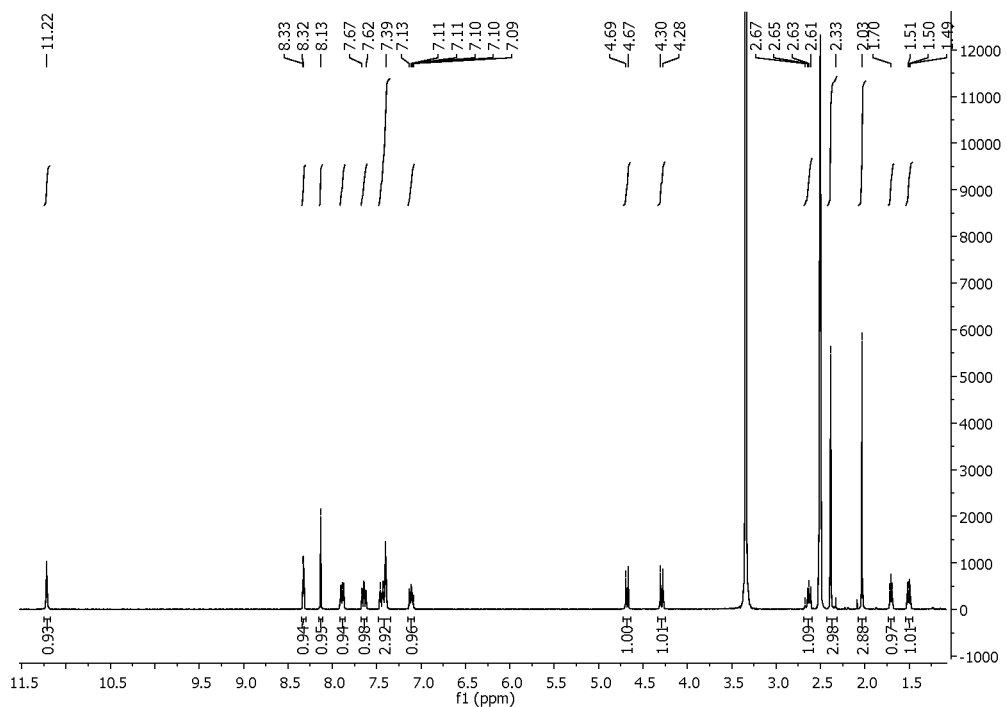
FIG. 4 shows a $^1$H NMR spectrum of Form CS2 in Example 1.

The $^1$H NMR spectrum of Form CS2 is substantially as depicted in FIG. 4, and the corresponding data are: $^1$H NMR (400 MHz, DMSO) δ11.22 (s, 1H), 8.33 (d, J=3.0 Hz, 1H), 8.13 (s, 1H), 7.89 (dd, J=9.1, 4.1 Hz, 1H), 7.64 (td, J=8.7, 3.1 Hz, 1H), 7.48-7.35 (m, 3H), 7.11 (ddd, J=11.5, 6.0, 3.0 Hz, 1H), 4.68 (d, J=10.2 Hz, 1H), 4.29 (d, J=10.3 Hz, 1H), 2.64 (dd, J=15.7, 8.8 Hz, 1H), 2.36 (d, J=21.5 Hz, 3H), 2.03 (s, 3H), 1.74-1.67 (m, 1H), 1.50 (dd, J=8.0, 4.8 Hz, 1H).

TABLE 1

| 2θ | d spacing | Intensity % |
|---|---|---|
| 7.81 | 11.32 | 100.00 |
| 9.55 | 9.26 | 5.68 |
| 11.44 | 7.73 | 23.41 |
| 12.53 | 7.07 | 25.17 |
| 15.58 | 5.69 | 46.96 |
| 15.78 | 5.62 | 11.77 |
| 16.40 | 5.41 | 4.67 |
| 19.05 | 4.66 | 12.69 |
| 19.38 | 4.58 | 17.51 |
| 19.57 | 4.54 | 18.50 |
| 21.32 | 4.17 | 21.23 |
| 21.73 | 4.09 | 6.60 |
| 22.27 | 3.99 | 11.54 |
| 23.03 | 3.86 | 5.32 |
| 23.23 | 3.83 | 6.23 |
| 23.99 | 3.71 | 15.14 |
| 25.42 | 3.50 | 4.70 |
| 25.89 | 3.44 | 23.53 |
| 26.28 | 3.39 | 7.86 |
| 27.26 | 3.27 | 15.44 |
| 28.04 | 3.18 | 5.25 |
| 29.36 | 3.04 | 3.75 |
| 31.09 | 2.88 | 5.99 |
| 33.99 | 2.64 | 1.25 |

Example 2 Preparation of Form CS2 by Anti-Solvent Addition Method

Figure 5:
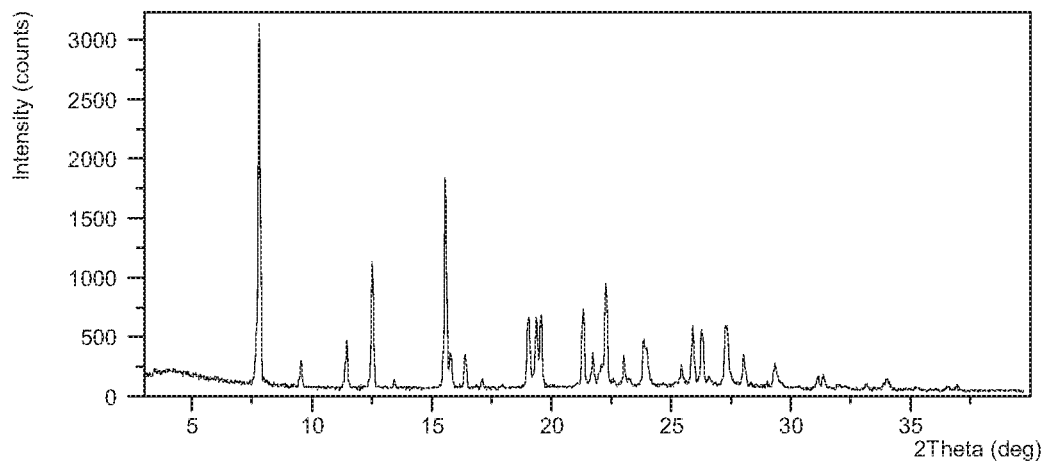
FIG. 5 shows an XRPD pattern of Form CS2 in Example 2.

Approximately 1026.0 mg of compound (I) was weighted and dissolved in 10.0 mL of methanol. The solution was filtered and stirred while adding about 10.0 mL of water as an anti-solvent. After stirred for about 4 hours, a large amount of solid precipitated out. The precipitation collected by suction filtration and dried under vacuum at 40° C. for about 18 hours to obtain solids. The obtained solid was confirmed to be Form CS2. The XRPD pattern is substantially as depicted in FIG. 5, and the XRPD data are listed in Table 2.

Figure 6:
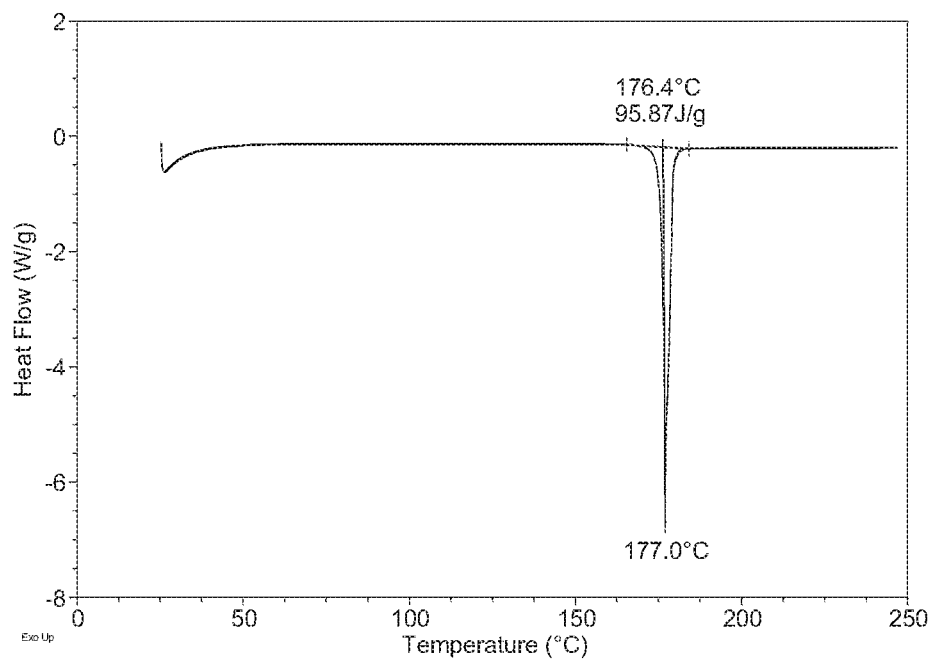
FIG. 6 shows a DSC curve of Form CS2 in Example 2.

The DSC curve of Form CS2 in this example is substantially as depicted in FIG. 6. When heated to 176° C., an endothermic peak appears, which corresponds to the melting endothermic peak of Form CS2.

Figure 7:
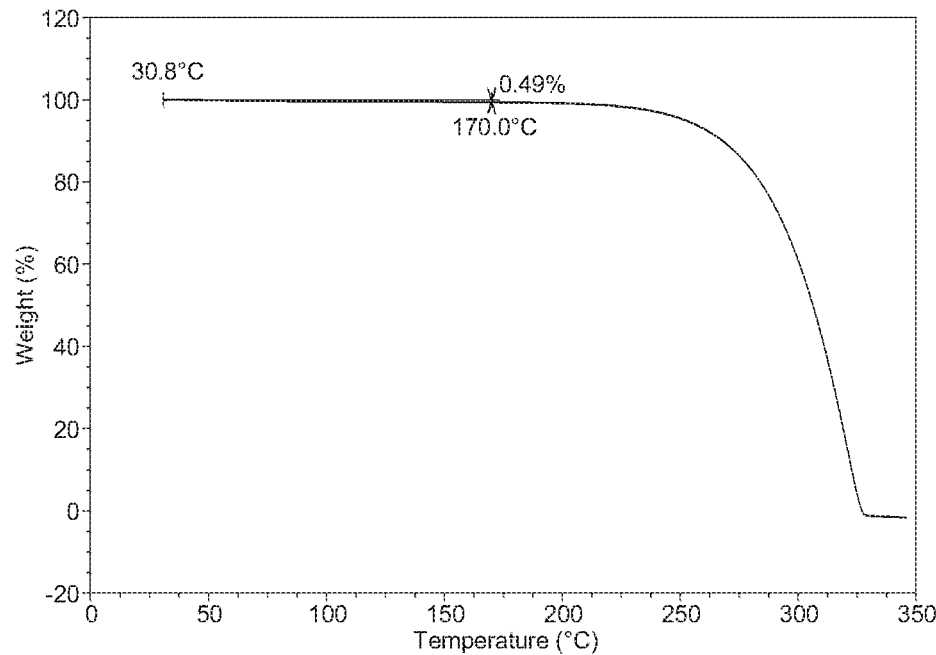
FIG. 7 shows a TGA curve of Form CS2 in Example 2.

The TGA curve of Form CS2 in this example shows about 0.5% weight loss when heated to 170° C., which is substantially as depicted in FIG. 7.

Figure 8:
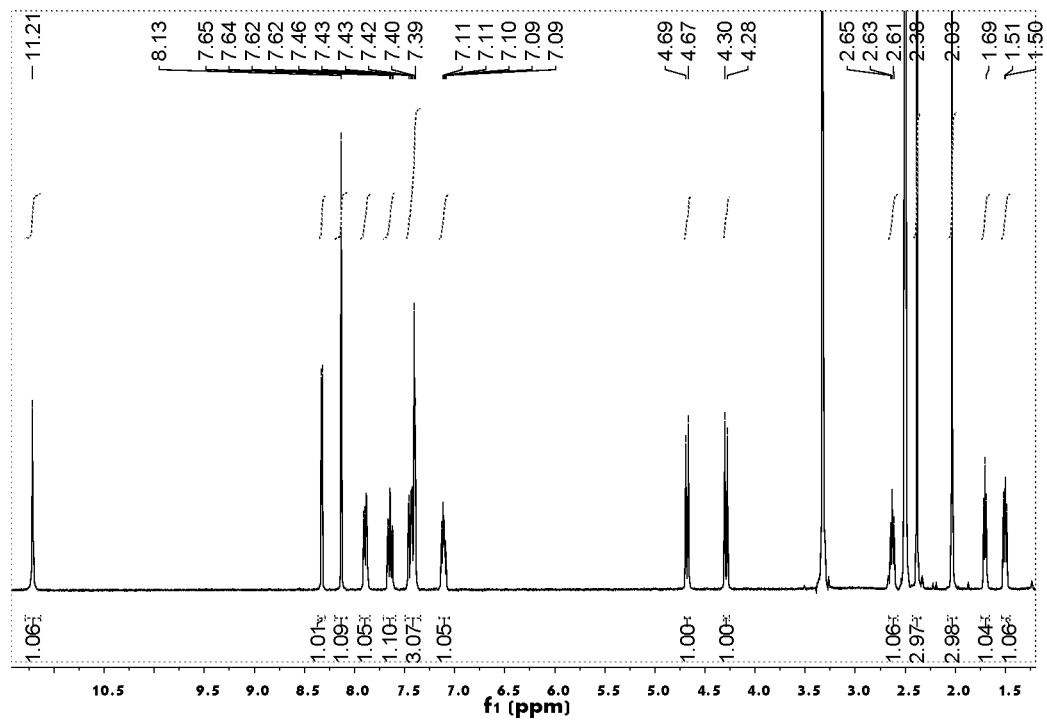
FIG. 8 shows a $^1$H NMR spectrum of Form CS2 in Example 2.

The $^1$H NMR spectrum of Form CS2 is substantially as depicted in FIG. 8, and the corresponding data are: $^1$H NMR (400 MHz, DMSO) δ11.21 (s, 1H), 8.33 (d, J=3.0 Hz, 1H), 8.13 (s, 1H), 7.89 (dd, J=9.2, 4.2 Hz, 1H), 7.64 (td, J=8.8, 3.1 Hz, 1H), 7.49-7.34 (m, 3H), 7.16-7.05 (m, 1H), 4.68 (d, J=10.2 Hz, 1H), 4.29 (d, J=10.3 Hz, 1H), 2.67-2.57 (m, 1H), 2.38 (s, 3H), 2.03 (s, 3H), 1.74-1.66 (m, 1H), 1.50 (dd, J=8.0, 4.8 Hz, 1H).

TABLE 2

| 2θ | d spacing | Intensity % |
|---|---|---|
| 7.84 | 11.27 | 100.00 |
| 9.59 | 9.22 | 6.98 |
| 11.49 | 7.70 | 13.05 |
| 12.56 | 7.05 | 35.00 |
| 15.61 | 5.68 | 59.13 |
| 15.82 | 5.60 | 9.92 |
| 16.44 | 5.39 | 9.29 |
| 19.07 | 4.65 | 19.61 |
| 19.41 | 4.57 | 19.56 |
| 19.60 | 4.53 | 20.52 |

TABLE 2-continued

| 2θ | d spacing | Intensity % |
|---|---|---|
| 21.36 | 4.16 | 22.18 |
| 21.77 | 4.08 | 10.04 |
| 22.31 | 3.98 | 29.55 |
| 23.07 | 3.86 | 9.34 |
| 23.89 | 3.72 | 14.02 |
| 24.00 | 3.71 | 11.54 |
| 25.46 | 3.50 | 6.67 |
| 25.93 | 3.44 | 17.57 |
| 26.31 | 3.39 | 16.60 |
| 27.33 | 3.26 | 16.63 |
| 28.06 | 3.18 | 9.34 |
| 29.37 | 3.04 | 7.28 |
| 31.15 | 2.87 | 3.40 |
| 31.38 | 2.85 | 4.42 |
| 29.37 | 3.04 | 7.28 |
| 31.15 | 2.87 | 3.40 |

Example 3-5 Preparation of Form CS2 by Ionic Liquid Induced Evaporation

Approximately 31.5 mg of compound (I) was dissolved in 1.0 mL of acetonitrile and filtered. A small amount of ionic liquid as shown in Table 3 was added, and the solution was slowly evaporated at room temperature to obtain solid. The solid obtained in example 3-5 were labeled as samples 3-5 and confirmed to be Form CS2.

TABLE 3

| Example | Ionic liquid | Sample |
|---|---|---|
| 3 | 1-ethyl-3-methylimidazolium methyl sulfate | Sample 3 |
| 4 | 1-ethyl-3-methylimidazolium hexafluoroantimonate | Sample 4 |
| 5 | 1,3-dimethylimidazolium dimethyl phosphate | Sample 5 |

Example 6 Stability of Form CS2

Form CS2 of the present disclosure were weighed and stored under conditions of 25° C./60% RH, 40° C./75% RH, 60° C./75% RH and 80° C. in open dishes. Crystalline form and chemical impurity were checked by XRPD and HPLC, respectively. The results are shown in Table 4.

TABLE 4

Figure 9:
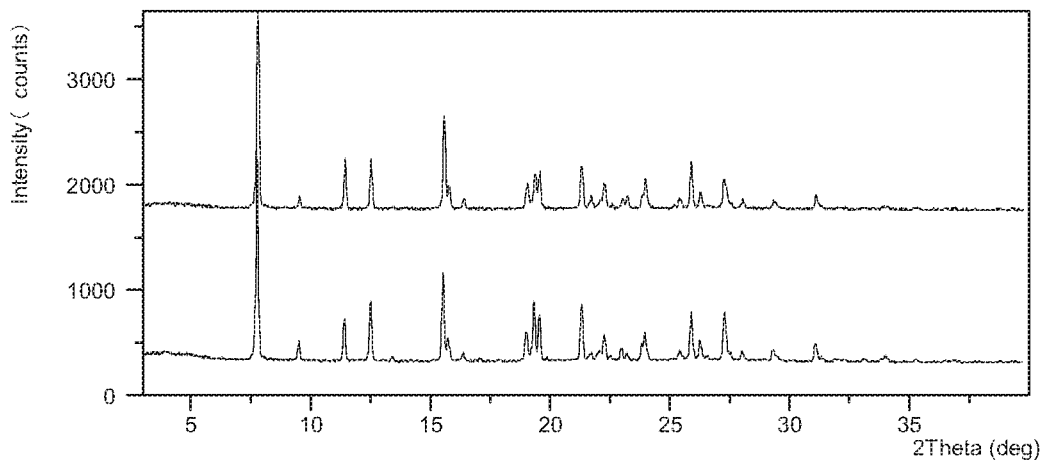
FIG. 9 shows an XRPD pattern overlay of Form CS2 before and after stored at 25° C./60% RH (top: before storage, bottom: after storage).
Figure 10:
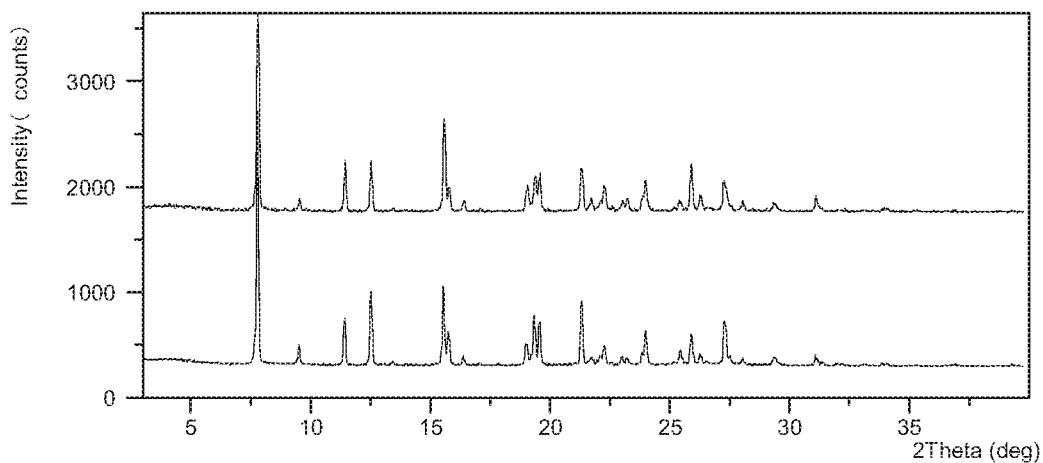
FIG. 10 shows an XRPD pattern overlay of Form CS2 before and after stored at 40° C./75% RH (top: before storage, bottom: after storage).
Figure 11:
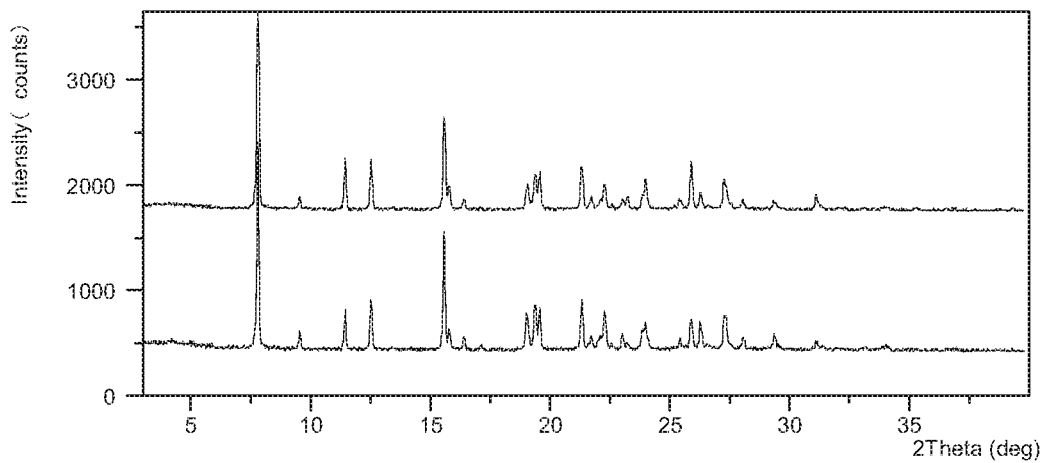
FIG. 11 shows an XRPD pattern overlay of Form CS2 before and after stored at 60° C./75% RH (top: before storage, bottom: after storage).

| Initial crystalline form | Initial purity | Storage condition | Storage time | Crystalline form after storage | Purity after storage |
|---|---|---|---|---|---|
| Form CS2 (top of FIG. 9) | 99.67% | 25° C./60% RH | 10 months | Form CS2 (bottom of FIG. 9) | 99.63% |
| Form CS2 (top of FIG. 10) | 99.67% | 40° C./75% RH | 10 months | Form CS2 (bottom of FIG. 10) | 99.67% |
| Form CS2 (top of FIG. 11) | 99.67% | 60° C./75% RH | 2 weeks | Form CS2 (bottom of FIG. 11) | 99.70% |

The results show that Form CS2 keeps stable for at least 10 months at 25° C./60% RH and 40° C./75% RH. Form CS2 keeps stable for at least 2 weeks at 60° C./75% RH, the purity of Form CS2 remained substantially unchanged. It can be seen that Form CS2 has good physical and chemical stability.

Example 7 Grinding Stability of Form CS2

Figure 12:
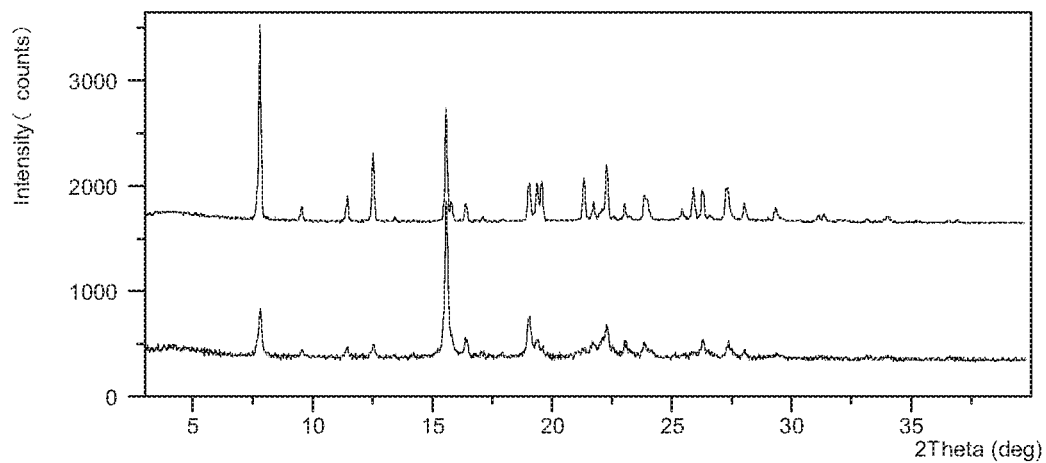
FIG. 12 shows an XRPD curve of Form CS2 before and after grinding (top: XRPD pattern before grinding; bottom: XRPD pattern after grinding).

Form CS2 was ground manually for 5 minutes in a mortar. The XRPD pattern of the solids before and after grinding are presented in FIG. 12 (top: XRPD pattern before grinding; bottom: XRPD pattern after grinding). The results show that the crystalline form of Form CS2 does not change after grinding. Form CS2 has good grinding stability.

Example 8 Hygroscopicity of Form CS2

Figure 13:
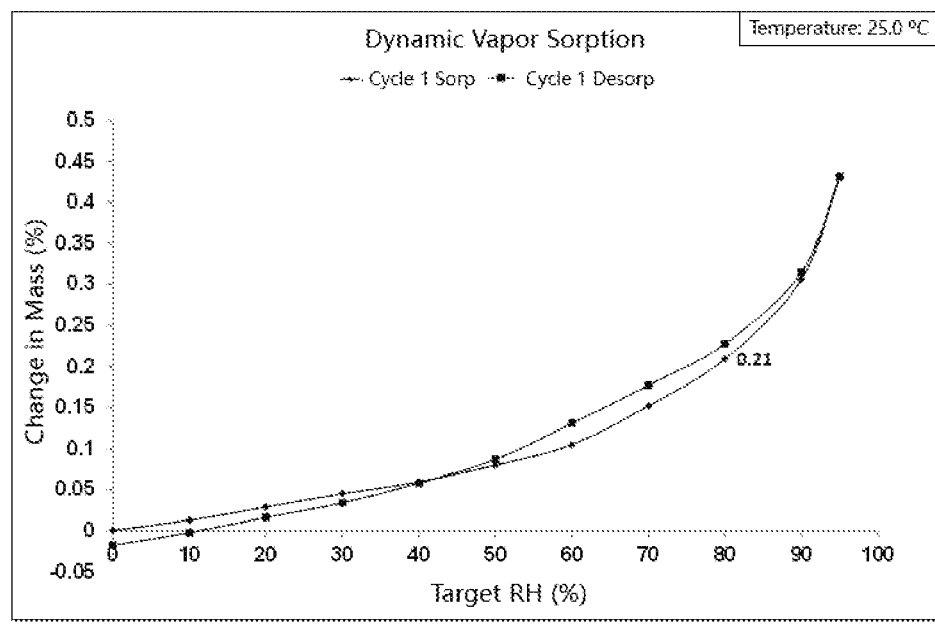
FIG. 13 shows a DSC curve of Form CS2.
Figure 14:
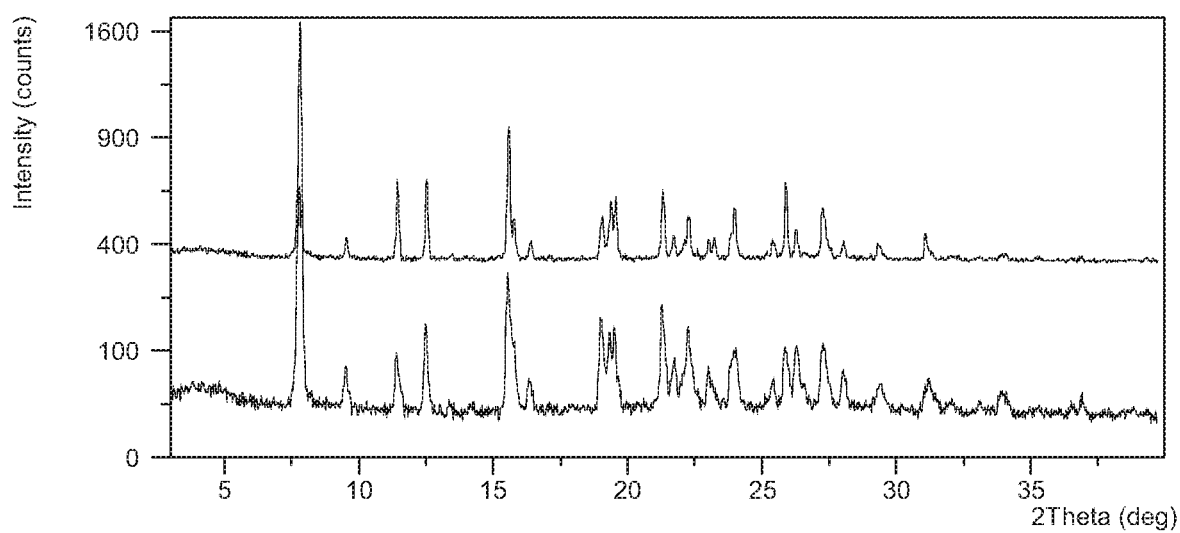
FIG. 14 shows an XRPD pattern overlay of Form CS2 before and after DVS test (top: XRPD pattern before DVS; bottom: XRPD pattern after DVS).

Dynamic vapor sorption (DVS) was applied to measure hygroscopicity of Form CS2 with about 10 mg of samples. The weight gains at each relative humidity were recorded in a cycle of 0-95%-0 RH. DVS is substantially as depicted in FIG. 13, and the experimental results are shown in Table 5. The XRPD pattern overlay of Form CS2 before and after DVS test is presented in FIG. 14 (top: XRPD pattern before DVS; bottom: XRPD pattern after DVS). The results show that the hygroscopicity of Form CS2 is low. The weight gain under 80% RH is 0.21%. Form CS2 is slightly hygroscopic. The crystalline form of Form CS2 does not change after DVS, which indicates that Form CS2 is physically stable at 0%-95% RH.

TABLE 5

| | Relative Humidity | |
|---|---|---|
| Weight Gain (%) | Weight gain under 80% Relative Humidity | Hygroscopicity |
| Form CS2 | 0.21% | Slightly hygroscopic |

Description and definition of hygroscopicity (Chinese Pharmacopoeia 2015 edition appendix Drug hygroscopic test guidelines, test at 25° C.±1° C., 80% RH.).
  deliquescent: Sufficient water is absorbed to form a liquid;
  very hygroscopic: Increase in mass is equal to or greater than 15 percent;
  hygroscopic: Increase in mass is less than 15 percent and equal to or greater than 2 percent;
  slightly hygroscopic: Increase in mass is less than 2 percent and equal to or greater than 0.2 percent.
  non hygroscopic or almost non hygroscopic: Increase in mass is less than 0.2%.

Example 9 Flowability Comparison of Form CS2 and the Prior Art Solid

Compressibility, also known as compressibility index is usually used to evaluate the flowability of powder and granular intermediates during the formulation process. A certain amount of powder was added into a measuring cylinder and bulk volume was recorded. Then the measuring cylinder was tapped to make the powder in the tightest state and the tapped volume was recorded. The bulk density ($\rho_0$), tapped density ($\rho_f$) were calculated, and compressibility index was calculated according to $c=(\rho_f-\rho_0)/\rho_f$. Compressibility index or Carr Index is an important indicator for evaluating the flowability of powder.

Compressibility index test method is as follows: Compressibility index was calculated according to bulk density $\rho_0$ and tapped density $\rho_f$ of Form CS2 and the amorphous solid of the prior art with $c=(\rho_f-\rho_0)/\rho_f*100\%$. Criteria of flowability is shown in Table 6.

TABLE 6

| Compressibility index (%) | Flowability |
|---|---|
| ≤10 | Excellent |
| 11-15 | Good |
| 16-20 | Fair |
| 21-25 | Passable |
| 26-31 | poor |
| 32-37 | Very poor |
| >38 | Very, very poor |

Amorphous solid was obtained by repeating the preparation method disclosed in CN103153963B. Flowability evaluation results of Form CS2 and the amorphous solid are presented in table 7, which indicate that the flowability of Form CS2 is remarkably superior to that of the amorphous solid in the prior art.

TABLE 7

| Form | Bulk density ($\rho_0$, g/mL) | Tapped density ($\rho_f$, g/mL) | Compressibility index (%) | Flowability |
|---|---|---|---|---|
| Amorphous solid | 0.196 | 0.274 | 28 | Poor |
| Form CS2 | 0.263 | 0.351 | 25 | Passable |

Example 10 Adhesiveness of Form CS2

30 mg of Form CS2 was weighed and added into the dies of φ8 mm round tooling, tabletted at 10 KN and held for 30s. The amount of material sticking to the punch was weighed. The compression was repeated twice and the cumulative amount, maximum amount and average amount of material sticking to the punch during the compression process were recorded. Detailed experimental results are shown in Table 8.

TABLE 8

| Crystalline Form | Maximum amount (mg) | Average amount (mg) | Cumulative amount (mg) |
|---|---|---|---|
| CS2 | 0.74 | 0.22 | 0.44 |

Example 11 Compressibility of CS2

80 mg of Form CS2 was weighted and added into the dies of φ6 mm round tooling, compressed at 10 KN. The round tablet was stored in a desiccator for 24 hours until complete elastic recovery. Hardness (H) was tested with a tablet hardness tester. Diameter (D) and thickness (L) were tested with caliper. Tensile strength of the powder was calculated with the following formula: $T=2H/\pi DL$. Under a certain force, the greater the tensile strength, the better the compressibility. The results are presented in Table 9.

TABLE 9

| Form | Thickness (mm) | Diameter (mm) | Hardness (N) | Tensile strength (MPa) |
|---|---|---|---|---|
| CS2 | 2.40 | 6.06 | 8.4 | 0.37 |

Example 12 Residual Solvents of Form CS2 and the Prior Art Solid

Amorphous solid was obtained by repeating the preparation method disclosed in CN103153963B. Residual solvents of Form CS2 and the amorphous solid were tested. The results show that Form CS2 has no residual solvents, while the -heptane and ethyl acetate residue in the amorphous solid is 46596.16 ppm and 1260.01 pm, respectively. According to the guideline of the International Council for Harmonization (ICH) on residual solvents, both n-heptane and ethyl acetate belong to Class 3 solvents, and the residual solvent must not exceed 5000 ppm. It can be seen that the residue of n-heptane in the amorphous solid is much higher than the limits of ICH, and the amorphous not suitable for drug substance.

Example 13 CS2 Drug Product

1. Preparation of Compound (I) Tablets

Form CS2 and intragranular excipients in Table 10 were blended according to formulation and the blend was compressed with the target weight of 500 mg using a φ20 mm single punch manual press at 5±0.5 KN pressure. The above tablets were crushed, passed through a 20 mesh sieve, then blended uniformly with the extragranular excipients shown in Table 10, and the blend was compressed with a target weight of 120.0 mg using a φ7 mm single punch manual press at 5±0.5 KN pressure.

TABLE 10

| | Component | Quantity (mg/unit) | Mass ratio (%) |
|---|---|---|---|
| Intragranular excipients | E-2006 (Form CS2) | 10.00 | 8.3 |
| | Lactose monohydrate | 88.88 | 74.1 |
| | Hydroxypropyl cellulose | 3.60 | 3.0 |
| | Low substituted hydroxypropyl cellulose | 10.80 | 9.0 |
| | Magnesium stearate | 0.36 | 0.3 |
| | Total | 113.64 | 94.7 |
| Extragranular excipients | Low substituted hydroxypropyl cellulose | 6.00 | 5.0 |
| | Magnesium stearate | 0.36 | 0.3 |
| | Total | 120.00 | 100.0 |

2. Stability of Form CS2 in Drug Product

The tablets prepared above were packed in 35 cc HDPE bottles (one tablet per bottle) with 1 g desiccant. The bottles were sealed with a sealer. The bottles were stored under conditions of 25° C./60% RH and 40° C./75% RH for 1 month. Crystalline form of Form CS2 tablet was tested and the results show that the crystalline form of Form CS2 does not change. In addition, single and total impurity of Form CS2 remained substantially unchanged in storage. The results presented in Table 11 and 12 indicate that Form CS2 keeps physically and chemically stable in drug product.

TABLE 11

Physical stability of Form CS2 in drug product

| Sample | Condition | Time | API crystalline Form after storage |
|---|---|---|---|
| Tablet contains Form CS2 | 25° C./60% RH | 1 month | Form CS2 |
| | 40° C./75% RH | 1 month | Form CS2 |

TABLE 12

Chemical stability of Form CS2 in drug product

| Condition | Time | Initial largest single impurity (%) | Largest single impurity after storage (%) | Initial total impurity (%) | Total impurity after storage (%) | Single impurity change (%) | Total impurity change (%) |
|---|---|---|---|---|---|---|---|
| 25° C./60% RH | 1 month | 0.08 | 0.09 | 0.17 | 0.21 | 0.01 | 0.04 |
| 40° C./75% RH | 1 month | 0.08 | 0.08 | 0.17 | 0.20 | 0 | 0.03 |

Example 14 In Vitro Dissolution and Dissolution Rate of Form CS2

In vitro dissolution test was performed on Form CS2 tablet obtained from example 12. Dissolution method according to Chinese Pharmacopoeia 2015<0931> was used. The conditions are as follows:

Medium: 0.1 mol/L aqueous solution of hydrochloric acid
Method: Paddle
Volume: 900 mL
Speed: 50 rpm
Temperature: 37° C.

Figure 15:
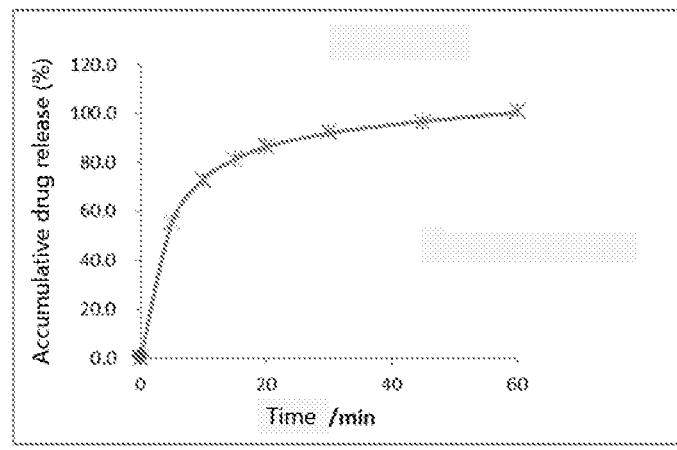
FIG. 15 shows an in vitro dissolution profile of Form CS2.

In vitro dissolution of Form CS2 are presented in Table 13 and FIG. 15.

TABLE 13

| Time (minute) | Cumulative drug release %<br>Form CS2 |
|---|---|
| 0 | 0.0 |
| 5 | 55.2 |
| 10 | 73.1 |
| 15 | 81.0 |
| 20 | 86.2 |
| 30 | 92.1 |
| 45 | 96.9 |
| 60 | 100.5 |

The results showed that Form CS2 drug product can undergo 100% dissolution in 0.1 mol/L aqueous hydrochloric acid, and the dissolution rate is high, which is favorable for achieving good in vivo bioavailability.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form CS2 of E-2006, wherein the X-ray powder diffraction pattern shows characteristic peaks at 2theta values of 7.8°±0.2°, 15.6°±0.2° and 11.4°±0.2° using CuKα radiation.

2. The crystalline form CS2 according to claim 1, wherein the X-ray powder diffraction pattern shows one or two or three characteristic peaks at 2theta values of 12.5°±0.2°, 21.3°±0.2° and 27.3°±0.2° using CuKα radiation.

3. The crystalline form CS2 according to claim 1, wherein the X-ray powder diffraction pattern shows one or two or three characteristic peaks at 2theta values of 24.0°±0.2°, 19.4°±0.2° and 22.3°±0.2° using CuKα radiation.

4. A process for preparing crystalline form CS2 according to claim 1, wherein the process comprises:
   (1) Dissolving compound (I) in a solvent to get a solution containing compound (I), then adding an anti-solvent to the solution slowly, stirring and crystallization to obtain crystalline form CS2; or
   (2) Dissolving compound (I) in ketones and slowly evaporating to obtain crystalline form CS2; or
   (3) Dissolving compound (I) in nitriles, adding an ionic liquid, then slowly evaporating to obtain crystalline form CS2.

5. The process for preparing crystalline form CS2 according to claim 4, wherein in method (1), said solvent is alcohol, said anti-solvent is water; in method (2), said ketone is acetone; in method (3), said nitrile is acetonitrile, said ionic liquid is 1-ethyl-3-methylimidazolium methyl sulfate, or 1-ethyl-3-methylimidazolium hexafluoroantimonate, or 1,3-dimethylimidazolium dimethyl phosphate.

6. The process for preparing crystalline form CS2 according to claim 5, wherein in method (1) said alcohol is methanol.

7. A pharmaceutical composition, said pharmaceutical composition comprises a therapeutically effective amount of crystalline form CS2 according to claim 1 and pharmaceutically acceptable carriers, diluents or excipients.

8. A method of treating insomnia and/or irregular sleep-wake rhythm disorder, comprising administering to a patient in need thereof a therapeutically effective amount of crystalline form CS2 according to claim 1.

* * * * *

(12) POST-GRANT REVIEW CERTIFICATE (287th)
United States Patent
Chen et al.

(10) Number: US 10,759,779 J1
(45) Certificate Issued: Jan. 31, 2025

(54) CRYSTALLINE FORM OF OREXIN RECEPTOR ANTAGONIST, PROCESSES FOR PREPARATION THEREOF AND USE THEREOF

(71) Applicants: Minhua Chen; Xiaoyu Zhang; Yanfeng Zhang; Chunxiang Huang

(72) Inventors: Minhua Chen; Xiaoyu Zhang; Yanfeng Zhang; Chunxiang Huang

(73) Assignee: BERGEN PHARMACEUTICAL LLC

Trial Number:

PGR2021-00047 filed Feb. 3, 2021

Post-Grant Review Certificate for:

Patent No.: 10,759,779
Issued: Sep. 1, 2020
Appl. No.: 16/777,121
Filed: Jan. 30, 2020

The results of PGR2021-00047 are reflected in this post-grant review certificate under 35 U.S.C. 328(b).

POST-GRANT REVIEW CERTIFICATE
U.S. Patent 10,759,779 J1
Trial No. PGR2021-00047
Certificate Issued Jan. 31, 2025

AS A RESULT OF THE POST-GRANT REVIEW PROCEEDING, IT HAS BEEN DETERMINED THAT:

Claims 1-4, 7 and 8 are cancelled.

\* \* \* \* \*